United States Patent [19]

Arakawa et al.

[11] Patent Number: 4,961,347
[45] Date of Patent: Oct. 9, 1990

[54] PROBE FOR ULTRASONIC FLAW DETECTORS

[75] Inventors: Takahiro Arakawa, Yokosuka; Kazuo Yoshikawa, Yokohama; Yoshimichi Atsuta, Yokosuka, all of Japan

[73] Assignee: Ishikawajima-Harima Heavy Industries Co., Ltd., Tokyo, Japan

[21] Appl. No.: 408,452

[22] Filed: Sep. 15, 1989

Related U.S. Application Data

[63] Continuation of Ser. No. 126,335, Nov. 30, 1987.

[51] Int. Cl.$^5$ ............................................. G01N 29/00
[52] U.S. Cl. ...................................................... 73/644
[58] Field of Search .................. 73/644, 658; 310/336, 310/363; 29/25.35

[56] References Cited

U.S. PATENT DOCUMENTS

| | | | |
|---|---|---|---|
| 2,697,936 | 12/1954 | Farrow | 310/336 |
| 3,177,381 | 4/1965 | Bosselaar | 310/336 |
| 3,350,923 | 11/1967 | Cross | 73/644 |
| 3,963,454 | 6/1976 | Singleton, Jr. | 420/546 |
| 4,040,822 | 8/1977 | Stern | 420/546 |
| 4,166,967 | 9/1979 | Benes et al. | 310/334 |
| 4,464,442 | 8/1984 | McDonald et al. | 420/546 |
| 4,505,160 | 3/1985 | Zacharias, Jr. | 310/336 |
| 4,703,656 | 11/1987 | Bhardwaj | 310/336 |

Primary Examiner—Hezron E. Williams
Assistant Examiner—Louis M. Arana
Attorney, Agent, or Firm—Dykema Gossett

[57] ABSTRACT

A probe for ultrasonic flaw detectors includes a transducer and either a protection plate to protect the transducer or a metallic part for attaching the transducer directly to the object to be tested for flaws, these two parts being bonded to each other with a heat-resisting brazing or soldering material. Because of its high bonding strength, the probe thus formed is not only capable of serving both in high and low temperature ranges, but also may be used in a roving mode or in a stationary mode in testing the object.

12 Claims, 2 Drawing Sheets

PROBE FOR ULTRASONIC FLAW DETECTORS

This is a continuation of copending application Ser. No. 07/126,335 filed on Nov. 30, 1987, now abandoned.

BACKGROUND OF THE INVENTION

1. Technical Field

The present invention generally relates to a probe for ultrasonic flaw detectors, and more particularly to a probe having an allowable service temperature limit greatly extended both in the high temperature and in the low temperature directions.

2. Background Art

Recently, along with the general trend of prolonging the service lifetime of various types of structures, the need to measure the degree of aging of such structures is increasing. Ultrasonic apparatus offers an effective means of assessing the remaining lifetime of these structures, in terms of the fatigue of the structure.

The conventional normal scan probe or a straight beam testing probe for such an ultrasonic apparatus is exemplified in FIG. 5 of the accompanying drawings, where the probe b is in slidable contact with the object or structure a to be tested, through a couplant, such as, for example, water or glycerol. The probe b is constructed by bonding a transducer f, which is made from an oscillator crystal, such as $Pb(Zr, Ti)O_3$, and which is sandwiched between a pair of electrodes e made by baking silver thereon at a low temperature of about 300 degrees C., onto a ceramic protection plate d, which comes in contact with the structure being tested through couplant c, with an epoxy type resin adhesive g.

The type of probe b, described above, is undesirable in that, when the structure a is one which may be heated to a high temperature, such as a nuclear reactor pressure vessel, the adhesive g is liable to separate under thermal expansion of the ceramic protection plate d, thereby limiting the allowable service temperature of the probe b to 150-200 degrees C., and restricting the application to those objects which will not become too hot.

When the structure is one which may become too cold, on the other hand, separation of adhesive g is also liable to occur upon contraction of the ceramic protection plate d, thus limiting cold temperature applications.

SUMMARY OF THE INVENTION

This invention is intended to eliminate the difficulties mentioned above.

Namely, it is an objective of this invention to provide a probe for ultrasonic flaw detectors that has an allowable service temperature limit which is extended in both the high and low temperature ranges.

Another objective of this invention is to provide a probe for ultrasonic flaw detectors that is slidable on the object or structure to be tested, or can be used in a roving mode to test the object.

Yet another objective of this invention is to provide a probe for ultrasonic flaw detectors that can be used in a stationary mode in testing the object.

The first and second objectives set forth above are achieved by a probe that is constructed by laminating a pair of electrodes, a transducer sandwiched therebetween, and a protection plate which is intended to contact the object to be tested through a couplant, so as not only to have the transducer and the two sandwiching electrodes unified into an integral body but also to have the body brazed or soldered to the protection plate, with the electrodes being of a heat-resisting type.

As a result of the above mentioned construction, in which the heat-resisting electrode is disposed between the protection plate and the transducer and integrally brazed thereonto, the bonding strength is raised, the allowable service temperature range of the probe is greatly increased in both the high temperature and low temperature ranges, and the reliability is improved.

Also, since a material is used for brazing that has an acoustic impedance (i.e., the product of sound velocity and the density) which is much closer to that of the transducer, as compared with adhesives whose acoustic impedance differ greatly therefrom, the ultrasonic properties such as sensitivity of flaw detection are also improved.

Furthermore, since a construction as described above allows free motion of the protection plate as attached, or coupled, to the object being tested by a couplant, it is suited for use in a roving mode flaw detection.

On the other hand, the above mentioned first and third objectives are achieved by a probe that is formed by laminating the pair of electrodes with the transducer sandwiched therebetween, these three being unified into an integral body, on a metallic part that is to be attached directly to the object to be tested. Since the metallic part is directly attached to the object to be tested, thus fixing the probe thereto, it is suited for use in a stationary mode of flaw detection.

DESCRIPTION OF THE PREFERRED EMBODIMENTS

The preferred embodiments of the probe for ultrasonic flaw detectors according to this invention will now be described with reference to the attached drawings.

Figure 1:
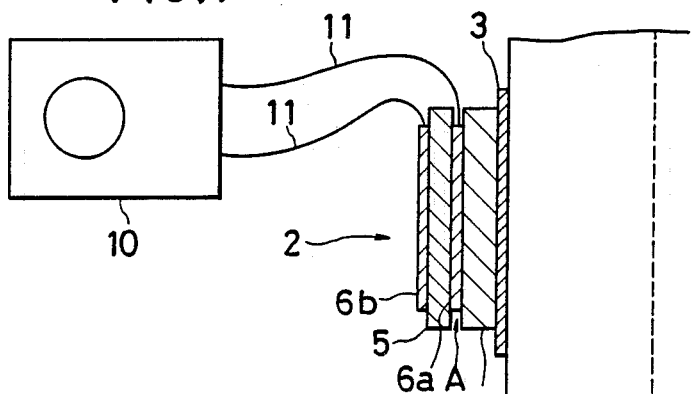
FIG. 1 is a schematic cross sectional view showing a preferred embodiment of the probe for ultrasonic flaw detectors of this invention.

In FIG. 1, numeral 1 stands for the object to be tested for flaws, which may be a high temperature structure, such as a nuclear reactor pressure vessel. For testing this object 1, there is provided a probe 2 of an ultrasonic flaw detector 10 in order to detect degradation or aggravation of the object 1. The ultrasonic flaw detector 10 operates such that it sends off ultrasonic waves from the probe 2 into the object 1 and converts the sound pressures of resulting echoes, which vary depending on the size of flaws, into electric signals, which are then displayed on a cathode ray tube in terms of voltage.

In the present preferred embodiment, the contact, or coupling, of the probe 2 to the object 1 is made through a couplant 3, which may be, for example, silicone oil or molten Pb, or can even be liquid Na, if the object 1 is a fast breeder reactor. In the case of silicone oil, it may be painted on the object's surface and in the case of liquid Na the reactor may be dipped in liquid Na.

The probe 2 comprises a transducer 5, a protection plate 4, which not only contacts the object 1 through the couplant 3 but protects the transducer 5 from mechanical and thermal effects, and a pair of electrodes 6a and 6b, which are formed integrally with the transducer 5, and from which a pair of Pt wires 11 extend to connect the probe 2 to the flaw detector 10. The protection plate 4 may be eliminated if the transducer 5 is sufficiently strong mechanically and thermally.

One important point here is that the electrode 6a formed of brazing material is provided between the transducer 5 and the protection plate 4 so as to bond these two by brazing them and to function as a heat-resisting electrode layer A.

For this purpose, a brazing material of Al-Si-Mg alloy (Si: 11.0 13.0%, Fe: 0.8% or less, Cu: 0.25% or less, Mn: 0.10% or less, Mg: 1.0 2.0%) is used. This brazing material is such that, by reducing the oxygen in the transducer 5 with its Al and Mg, brazing of ceramic to metal has been made possible for the first time. Si in this brazing material functions to lower the melting point, and as such may be replaced with Sn or other similar elements.

Furthermore, the other electrode 6b is made from the same brazing material, and a pair of Pt wires 11 are also attached to the electrodes 6a and 6b with the same material.

Experiments have shown that a heat-resisting electrode layer A brazed in an Ar atmosphere at a temperatures of 480 degrees C., for 30 minutes and under a pressure of 0.02 kgf/mm$^2$ is capable of raising the allowable service temperature of the probe 2 to as high as 550–600 degrees C. Also, in a durability test, which has been continuously conducted for about one year in a furnace held at 335 degrees C., no anomalies, such as separation, have been detected.

In the case described above, high temperature structures such as nuclear reactor pressure vessel for the test object 1 were given as examples, however, owing to its great bonding strength, the present probe 2 may be applied to low temperature structures, such as LNG tanks; and in fact, there is an advantage in applying it to LNG tanks, using LNG itself as the couplant 3. This has been verified by an experiment conducted in liquid nitrogen (−196 degrees C.), in which no separation had taken place.

Also it is quite feasible, due to the high bonding strength mentioned above, to apply the probe 2 of this invention to space structures, such as a space station whose temperatures vary inordinately when alternately subjected to direct irradiation of the sun and the shade.

As a further application of the principles of this invention described above, silver-alloy brazing was tried. Specifically, in the embodiment having a single crystal of lithium niobate (LiNbO$_3$) as the transducer 5, and with a cermet plate as the protection plate 4, the bonding surfaces of the transducer 5 and the protection 4 were provided with a thin film of Cu or Ni, formed thereat by ion plating and then were subjected to a heat treatment of 800 degrees C. for 1 hour so as to strengthen the bonding of the thin films thus formed on the transducer 5 and the protection plate 4. Subsequently, brazing was conducted in the Ar atmosphere at 680 degrees C. for 15 minutes at 0.02 kgf/mm$^2$ with a silver-alloy (Ag: 45%, Cu: 16%, Cd: 24%: Zn: substantially the remainder) as the brazing material. This method also produced a probe 2 which was quite satisfactory both at high and low temperatures.

Thus, by forming a heat-resisting electrode layer A of, for example, Al-base alloy, Ag-base alloy, Pb-base alloy or the like as the electrode 6a between the transducer 5 and the protection plate, with 6a, 5 and 4 being brazed, the upper and the lower limits of allowable temperature of the probe 2 can be greatly raised and lowered, respectively, thereby increasing the range of applications of the probe 2.

Figure 2:
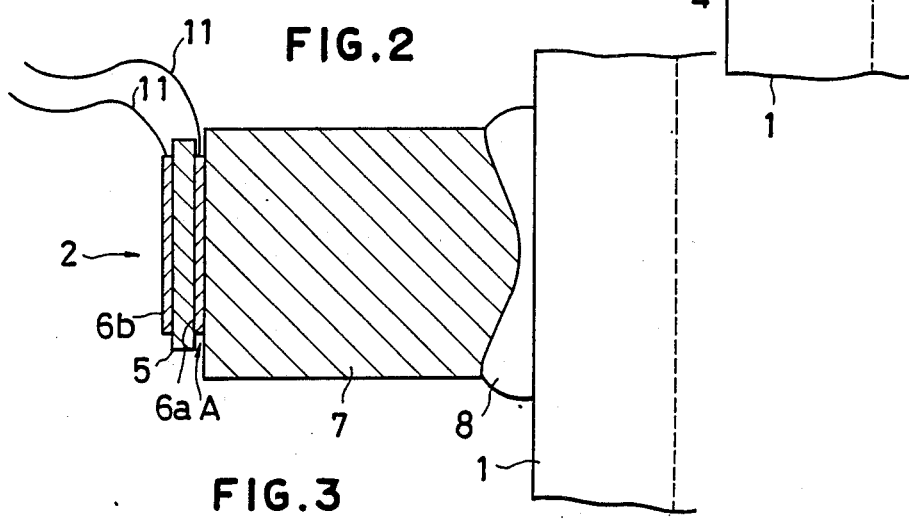
FIG. 2 is a schematic cross sectional view showing another preferred embodiment.
Figure 3:
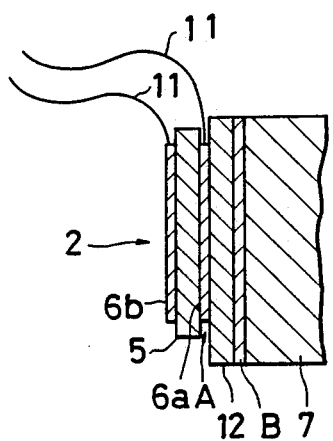
FIG. 3 is a partial schematic cross sectional view showing an application of the embodiment of FIG. 2.

FIGS. 2 and 3 depict other preferred embodiments of this invention. In the preferred embodiment illustrated in FIG. 2, there is provided a metallic cylinder 7 through which the ultrasonic waves can propagate. A heat-resisting electrode layer A is formed between the metallic cylinder 7 and the transducer 5 by brazing these two materials 5 and 7 along with the electrode 6a into a unified integral body. Another electrode 6b is brazed on the other side of the transducer 5. Here, the conditions of brazing the metallic part 7 and the transducer 5 are much the same as the foregoing example, except that, when the silver-alloy brazing is used, the ion plating on the metallic part 7 may be dispensed with.

The type of metallic material for the metallic part 7, should be amenable to bonding to the testing object 1 and should possess an acoustic impedance that is approximately the same as that of the object 1. For example, when the test object 1 is a nuclear reactor pressure vessel, which is generally made from steels, mild steel is used for a metallic part 7. When the object 1 is a space station, which is constructed from various metallic materials, a metal that is suited to the particular part should be selected therefor.

The metallic part 7 is welded to the test object 1 by a weldment 8, as by arc welding although other welding methods, such as stud welding, can be used.

Furthermore, inasmuch as the sole reason for using the metallic part 7 is that direct welding of the ceramic transducer 5 onto the test object 1 is difficult, it is clear that the metallic part 7 is employed merely for the sake of convenience of welding. The shape of the metallic part 7 therefore need not be limited to a cylinder. Also, although a long piece is preferably for the metallic part 7 because of the function of relieving thermal stresses by radiation effect, this is not a necessary requirement.

In another application, the transducer 5 is brazed to the metallic attachment 7 beforehand, and the cylinder 7 accompanying the transducer 5 is welded to the test object 1 at the construction site so as to permit monitoring of the object. For example, the probe 2 of this invention may well be used for monitoring the changes in the bearing wall thickness of an LNG pump immersed in an LNG tank so as to detect anomalous rotation of the pump. As another example, the probe 2 of this invention may equally well be used for monitoring the changes in the wall thickness in a high temperature structure at portions that are subjected to severe wear.

FIG. 3 shows a further application of the embodiment of FIG. 2, in which a cermet plate 12 is disposed between the transducer 5 and the metallic part 7, which is made of mild steel, and the bonding between the cermet plate 12 and the transducer 5, and between the cermet plate 12 and the metallic cylinder 7 are made by brazing with A and B of the aforementioned Al-base, for example, heat-resisting brazing material. Due to this construction, the appreciable difference in the thermal expansion coefficient which exists between the mild steel constituting the metallic part 7 and the lithium niobate transducer 5 is effectively alleviated by employing cermet, which is a substance that is intermediate between metals and ceramics, in between the two parts so that the bonding therebetween is ensured.

Figure 4:
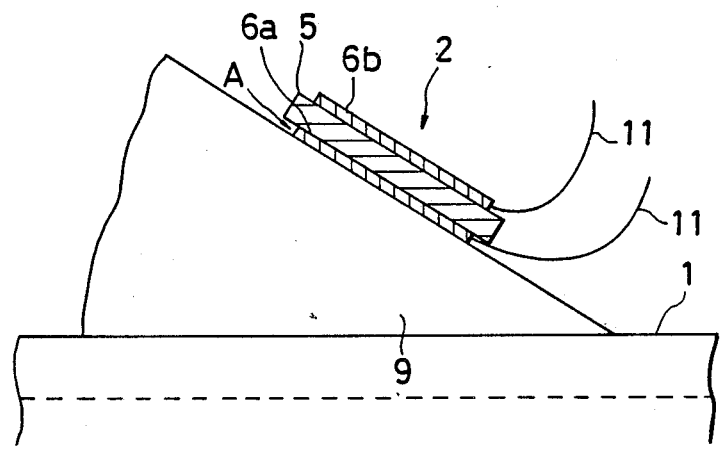
FIG. 4 is a schematic cross sectional view showing yet another preferred embodiment.
Figure 5:
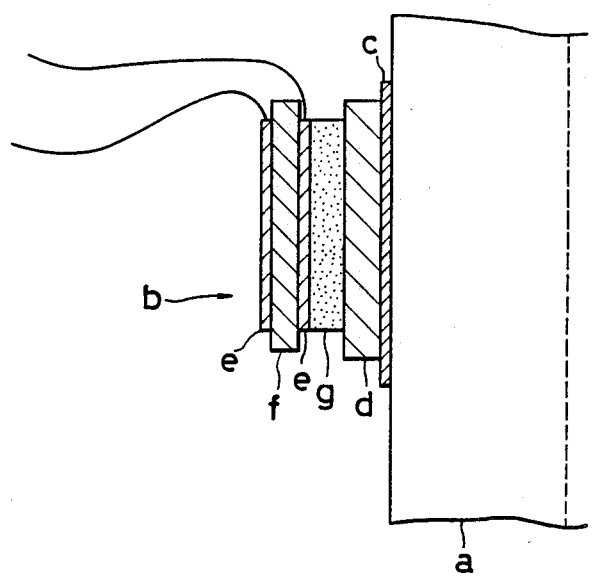
FIG. 5 is a schematic cross sectional view showing a conventional probe for ultrasonic flaw detectors.

Although a normal scan probe has been explained in the foregoing examples, an angle probe can be used instead. For example, in a case similar to that described in FIG. 2, the metallic material may be attached obliquely to the object 1 so that the ultrasonic waves are introduced obliquely into the object 1 during monitoring of the magnitude of flaws such as cracks. FIG. 4 illustrates another example. In this case, a wedge 9 is provided between the probe 2 and the object 1 so as to obliquely attach the probe 2 to the object 1.

Finally, even though brazing was the sole method of bonding given in the foregoing example, soldering may be used equally well if and when the intended service temperature permits such material.

We claim:

1. A probe for an ultrasonic flaw detector, comprising:
   a transducer assembly having a transducer made from lithium niobate, said transducer being sandwiched between a pair of electrodes; and
   an element disposed between said transducer assembly and an object to be tested for flaws;
   at least one of said electrodes being an Ag-based brazing alloy, said at least one electrode being brazed so as to integrally join said transducer assembly and said element;
   a bonding surface being defined on a face of said transducer facing said at least one electrode, said bonding surface having a thin film of Cu or Ni formed thereon by a surface treatment and heat treatment at 800° C. for about one hour.

2. A probe for an ultrasonic flaw detector according to claim 1, wherein said surface treatment is an ion plating.

3. A probe for an ultrasonic flaw detector according to claim 1, wherein said element is a cermet plate.

4. A probe for an ultrasonic flaw detector according to claim 1, wherein said Ag-based brazing alloy contains 45% Ag, 16% Cu, 24% Cd and the remainder being Zn.

5. A probe for an ultrasonic flaw detector according to claim 1, wherein said element is a metallic member of a material selected to have an acoustic impedance approximately equal to that of the object to be tested.

6. A probe for an ultrasonic flaw detector according to claim 5, wherein said metallic member is cylindrical.

7. A probe for an ultrasonic flaw detector, comprising:
   a transducer assembly having a transducer made from lithium niobate, said transducer being sandwiched between a pair of electrodes; and,
   an element disposed between said transducer assembly and an object to be tested for flaws,
   said pair of electrodes each being formed from an Al-based brazing alloy and which are each integrally joined to said transducer by brazing, the resulting probe withstanding temperatures up to 550° C. without any cooling being required, and wherein said Al-based alloy contains 11.0–13.0% Si, 0.8% or less Fe, 0.25% or less Cu, less than 0.10% Mn and 1.0–2.0% Mg.

8. A probe for an ultrasonic flaw detector, comprising:
   a transducer assembly having a transducer made from lithium niobate, said transducer being sandwiched between a pair of electrodes; and
   a cermet plate disposed between said transducer assembly and an object to be tested for flaws, said pair of electrodes each being formed from an Al-based brazing alloy containing 11.0–13.0% Si, 0.8% or less Fe, 0.25% or less Cu, less than 0.10% Mn and 1.0–2.0% Mg, and wherein said electrodes are each integrally joined to said transducer by brazing, the resulting probe withstanding temperatures up to 550° C. without any cooling being required.

9. A method of constructing a probe for use as an ultrasonic flaw detector, comprising the steps of:
   (A) sandwiching a lithium niobate transducer between a pair of electrodes formed from a brazing material;
   (B) applying a thin film of Cu or Ni to bonding surfaces respectively of the transducer and a protective element;
   (C) then, heat treating said transducer and said protective element at a temperature of about 800 degrees C. for about one hour;
   (D) then, brazing said transducer to said protective element.

10. The method of claim 9, including the step of welding the protective element to an object to be tested.

11. The method of claim 9, wherein step (B) is performed by a surface treatment.

12. The method of claim 11, wherein the surface treatment is ion plating.

* * * * *